(12) United States Patent
Pevarello et al.

(10) Patent No.: US 6,306,903 B1
(45) Date of Patent: Oct. 23, 2001

(54) ALPHA-AMINOAMIDE DERIVATIVES USEFUL AS ANALGESIC AGENTS

(75) Inventors: Paolo Pevarello, Pavia; Mario Varasi, Milan; Patricia Salvati, Arese, all of (IT); Claes Post, Sigtuna (SE)

(73) Assignee: Newron Pharmaceuticals S.p.A., Gerenzano (IT)

( * ) Notice: Subject to any disclaimer, the term of this patent is extended or adjusted under 35 U.S.C. 154(b) by 0 days.

(21) Appl. No.: 09/582,198

(22) PCT Filed: Dec. 12, 1998

(86) PCT No.: PCT/EP98/08157

§ 371 Date: Aug. 29, 2000

§ 102(e) Date: Aug. 29, 2000

(87) PCT Pub. No.: WO99/35125

PCT Pub. Date: Jul. 15, 1999

(30) Foreign Application Priority Data

Dec. 31, 1997 (GB) .................................................. 9727523

(51) Int. Cl.$^7$ ...................... A61K 31/275; A61K 31/165; C07C 255/50; C07C 233/05
(52) U.S. Cl. ........................... 514/522; 514/619; 514/620; 558/414; 564/163; 564/164; 564/171
(58) Field of Search ..................................... 564/163, 164, 564/171; 558/414; 514/620, 619, 522

(56) References Cited

U.S. PATENT DOCUMENTS 5,945,454 * 8/1999 Paverello et al. .................... 514/620

FOREIGN PATENT DOCUMENTS

| 0 525 360 A | 2/1993 | (EP) . |
| 2 059 963 A | 4/1981 | (GB) . |
| WO90/14334 | 11/1990 | (WO) . |
| WO97/05102 | 2/1997 | (WO) . |

OTHER PUBLICATIONS

"Synthesis and Anticonvulsant Activity of a New Class of 2–(Arylalkyl) aminolalkanamide Derivatives", Pevarello et al, *Journal of Medicinal Chemistry*, vol. 41, No. 4, Feb. 12, 1998, pp 579–590.

* cited by examiner

Primary Examiner—Floyd D. Higel
Assistant Examiner—Ebenezer Sackey
(74) Attorney, Agent, or Firm—Arent Fox Kintner & Plotkin & Kahn, PLLC.

(57) ABSTRACT

The present invention relates to novel and known alpha-aminoamide compounds, to a process for their preparation, to pharmaceutical composition containing them and to their use as therapeutic agents.

In particular, the compounds of the present invention are endowed with analgesic properties and are particularly useful for the treatment and alleviation of chronic and neuropathic pain.

Accordingly, one object of the present invention is to provide the use of a compound of formula (I)

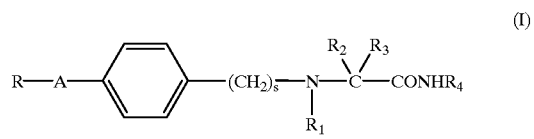

wherein:

A is a $-(CH_2)_m-$, $-(CH_2)_n-X-$ or $-(CH_2)_v-O-$ group wherein m is an integer of 1 to 4, n is zero or an integer of 1 to 4, X is $-S-$ or $-NH-$, and v is zero or an integer of 1 to 5;

s is 1 or 2;

R is a furyl, thienyl, or pyridyl ring or a phenyl ring optionally substituted by one or two substitutents independently chosen from halogen, cyano, $C_1-C_4$ alkyl, $C_1-C_4$ alkoxy and trifluoromethyl;

$R_1$ is hydrogen or $C_1-C_4$ alkyl;

one of $R_2$ and $R_3$ is hydrogen and the other is hydrogen or $C_1-C_4$ alkyl optionally substituted by hydroxy or phenyl; or $R_2$ and $R_3$ taken together with the carbon atom to which they are linked form a $C_3-C_6$ cycloalkyl ring; or $R_2$ and $R_3$ are both methyl;

$R_4$ is hydrogen or $C_1-C_4$ alkyl.

12 Claims, No Drawings

ALPHA-AMINOAMIDE DERIVATIVES USEFUL AS ANALGESIC AGENTS

This appln is a 371 of PCT/EP98/08157 filed Dec. 12, 1998.

The present invention relates to novel and known alpha-aminoamide compounds, to a process for their preparation, to pharmaceutical composition containing them and to their use as therapeutic agents.

In particular, the compounds of the present invention are endowed with analgesic properties and are particularly useful for the treatment and alleviation of chronic and neuropathic pain.

Chronic and neuropathic pain are associated with prolonged tissue damage or injuries to the peripheral or central nervous system and result from a number of complex changes in nociceptive pathways.

Clinical manifestations of chronic pain include a sensation of burning or electric shock, feelings of bodily distortion, allodynia and hyperpathia.

Despite the large number of available analgesics, their use is limited by severe side effects and modest activity in some pain conditions. Therefore there is still a clear need to develop new compounds.

International applications WO 90/14334, WO 94/22808, WO 97/05111 and WO 97/05102 disclose substituted benzylaminopropionamide compounds active on the central nervous system and useful as anti-epileptic, anti-Parkinson, neuroprotective, antidepressant, antispastic and hypnotic agents.

The present invention is based on the finding that compounds known from the above-cited international applications and new ones, closely related thereto, have analgesic properties in mammals, including humans.

Accordingly, one object of the present invention is to provide the use of a compound of formula (I)

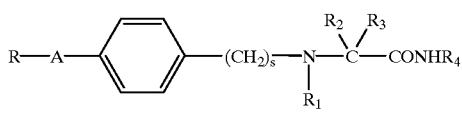

(I)

wherein:
A is a —$(CH_2)_m$—, —$(CH_2)_n$—X— or —$(CH_2)_v$—O— group wherein m is an integer of 1 to 4, n is zero or an integer of 1 to 4, X is —S— or —NH—, and v is zero or an integer of 1 to 5;
s is 1 or 2;
R is a furyl, thienyl, or pyridyl ring or a phenyl ring optionally substituted by one or two substitutents independently chosen from halogen, cyano, $C_1$–$C_4$ alkyl, $C_1$–$C_4$ alkoxy and trifluoromethyl;
$R_1$ is hydrogen or $C_1$–$C_4$ alkyl;
one of $R_2$ and $R_3$ is hydrogen and the other is hydrogen or $C_1$–$C_4$ alkyl optionally substituted by hydroxy or phenyl; or $R_2$ and $R_3$ taken together with the carbon atom to which they are linked form a $C_3$–$C_6$ cycloalkyl ring; or $R_2$ and $R_3$ are both methyl;
$R_4$ is hydrogen or $C_1$–$C_4$ alkyl;
or a pharmaceutically acceptable salt thereof;
and wherein
when A is a —$(CH_2)_5$—O— group then s is 1, R is a phenyl group optionally substituted by one or two substitutents selected independently from halogen, trifluoromethyl and $C_1$–$C_4$ alkoxy, $R_1$ is hydrogen and one of $R_2$ and $R_3$ is hydrogen and the other is hydrogen or $C_1$–$C_4$ alkyl optionally substituted hydroxy;
and wherein
when $R_2$ and $R_3$ are both methyl then R is other than furyl, thienyl or pyridyl ring, in the manufacture of a medicament for use as analgesic, in particular for the treatment and alleviation of chronic and neuropathic pain.

A —$(CH_2)_m$—, —$(CH_2)_n$— or —$(CH_2)_v$— chain may be a branched or straight chain. Alkyl and alkoxy groups may be branched or straight groups. Representative examples of $C_1$–$C_4$ alkyl groups include methyl, ethyl, n- and iso-propyl, n-, iso-, sec- and tert-butyl.

Representative examples of $C_1$–$C_4$ alkoxy groups include methoxy and ethoxy.

A $C_3$–$C_6$ cycloalkyl group is for instance cyclopropyl, cyclopentyl or cyclohexyl, in particular cyclopentyl or cyclohexyl.

A halogen atom is fluorine, bromine, chlorine or iodine, in particular, chlorine or fluorine.

Pharmaceutically acceptable salts of the compounds of the invention include acid addition salts with inorganic, e.g. nitric, hydrochloric, hydrobromic, sulphuric, perchloric and phosphoric acids or organic, e.g. acetic, trifluoroacetic, propionic, glycolic, lactic, oxalic, malonic, malic, maleic, tartaric, citric, benzoic, cinnamic, mandelic and salicylic acids.

The compounds of formula (I) have asymmetric carbon atoms and therefore they can exist either as racemic mixtures or as individual optical isomers (enantiomers).

Accordingly, the present invention also include within its scope all the possible isomers and their mixtures and both the metabolites and the pharmaceutically acceptable bio-precursors (otherwise known as pro-drugs) of the compounds of formula (I).

Preferred compounds of formula (I) are those wherein
A is a group chosen from —$CH_2$—, —$CH_2$—$CH_2$—, —$CH_2$—S—, —$CH_2$—$CH_2$—S— and —$(CH_2)_v$—O— in which v is an integer of 1 to 5;
s is 1 or 2;
R is a phenyl ring optionally substituted by one or two substitutents independently chosen from halogen and cyano or a thienyl ring;
$R_1$ is hydrogen or $C_1$–$C_4$ alkyl;
one of $R_2$ and $R_3$ is hydrogen and the other is $C_1$–$C_4$ alkyl optionally substituted by hydroxy or phenyl; or $R_2$ and $R_3$ are both methyl;
$R_4$ is hydrogen or $C_1$–$C_4$ alkyl; and the pharmaceutically acceptable salts thereof.

Examples of specific compounds of formula (I) are:
2-[4-(3-fluorobenzyloxy)benzylamino]-2-methyl-propanamide;
2-[4-(3-fluorobenzyloxy)benzylamino]propanamide;
2-([4-benzyloxybenzylamino)propanamide;
2-[4-(2-fluorobenzyloxy)benzylamino]propanamide;
2-[4-(4-fluorobenzyloxy)benzylamino]propanamide;
2-[4-(2-chlorobenzyloxy)benzylamino]propanamide;
2-(4-(3-chlorobenzyloxy)benzylamino]propanamide;
2-[4-(3-fluorobenzyloxy)benzylamino]-3-hydroxy-N-methylpropanamide;
2-[4-(2-fluorobenzyloxy)benzylamino]-3-hydroxy-N-methylpropanamide;
2-[4-(2-chlorobenzyloxy)benzylamino]-3-hydroxy-N-methylpropanamide;
2-[4-(3-cyanobenzyloxy)benzylamino]-3-hydroxy-N-methylpropanamide;

2-[4-(3-chlorobenzyloxy)phenylethylamino]-propanamide;
2-(4-benzyloxybenzylamino)-3-hydroxy-N-methyl-propanamide;
2-(4-(2-thenyloxy)benzylamino)-propanamide;
2-[4-(3-fluorobenzyloxy)benzylamino]-N-methylpropanamide;
2-[4-(3-fluorobenzyloxy)benzylamino]-3-hydroxy-propanamide;
2-[4-(2-(3-fluorophenyl)ethyloxy)benzylamino]-propanamide;
2-[4-(2-(3-fluorophenyl)ethyl)benzylamino]-propanamide;
2-[N-4-benzyloxybenzyl-N-methyl-amino]-propanamide;
2-[2-(4-(3-chlorobenzyloxy)phenylethyl)amino]-propanamide;
2-[4-benzylthiobenzylamino]-propanamide;
2-[4-(3-phenylpropyloxy)benzylamino]-propanamide;
2-[4-(4-phenylbutyloxy)benzylamino]-propanamide;
2-[4-(5-phenylpentyloxy)benzylamino]-propanamide;
2-[4-benzyloxybenzylamino]-3-phenyl-N-methylpropanamide;
2-[4-benzyloxybenzylamino]-3-methyl-N-methylbutanamide, if the case either as a single isomer or as a mixture thereof, and the pharmaceutically acceptable salts thereof.

An aspect of this invention relates to a pharmaceutically composition having analgesic activity, in particular against chronic and neuropathic pain, comprising a compound of formula (I), as herein defined, as an active agent and a pharmaceutically acceptable salt thereof.

A further aspect of this invention relates to a method of treating a mammal, including humans, in need of an analgesic agent, said method comprising administering thereto an effective amount of a compound of formula (I) or a pharmaceutically acceptable salt thereof.

Neuropathic and chronic pain conditions in a mammal can thus be alleviated and treated. Examples of pain conditions that can be treated by a compound of formula (I) include:
 peripheral neuropathies, such as trigeminal neuralgia, postherapeutic neuralgia, diabetic neuropathy, glossopharyngeal neuralgia, radiculopathy, and neuropathy secondary to metastatic infiltration, adiposis dolorosa and burn pain; and
 central pain conditions following stroke, thalamic lesions and multiple sclerosis. "Treatment" as used herein covers any treatment of a condition in a mammal, particularly a human, and includes:
  (i) preventing the disease from occurring in a subject which may be predisposed to the disease, but has not yet been diagnosed as having it;
  (ii) inhibiting the condition, i.e., arresting its development; or
  (iii) relieving the condition, i.e., causing regression of the disease.

Another object of the present invention are the novel compounds of formula (IA)

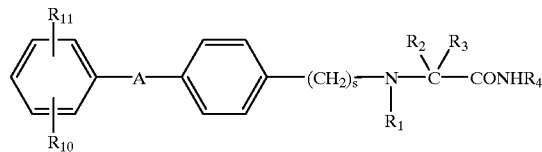

(IA)

wherein:
 A is a —(CH$_2$)$_m$— or —(CH$_2$)$_n$—E— group wherein m is an integer of 1 to 4, n is zero or an integer of 1 to 4 and E is —O—, —S— or —NH—;
 s is 1 or 2;
 one of $R_{10}$ and $R_{11}$ is cyano and the other is independently selected from hydrogen, halogen, cyano, $C_1$–$C_4$ alkyl, $C_1$–$C_4$ alkoxy and trifluoromethyl;
 $R_1$ is hydrogen or $C_1$–$C_4$ alkyl;
 one of $R_2$ and $R_3$ is hydrogen and the other is hydrogen or $C_1$–$C_4$ alkyl optionally substituted by hydroxy or phenyl; or $R_2$ and $R_3$ taken together with the carbon atom to which they are linked form a $C_3$–$C_6$ cycloalkyl ring; or $R_2$ and $R_3$ are both methyl;
 $R_4$ is hydrogen or $C_1$–$C_4$ alkyl; and the pharmaceutically acceptable salts.

The compounds of formula (IA) fall within the scope fo the compound of formula (I), as herein defined. Therefore all the definitions and biological properties stated above as to a compound of formula (I) apply also to a compound of formula (IA).

In particular, preferred compounds of formula (IA) are those wherein
 A is a group —CH$_2$—O— or —CH$_2$—CH$_2$—O—,
 s is 1;
 one of $R_{10}$ and $R_{11}$ is cyano and the other is hydrogen, cyano or halogen; and
 one of $R_2$ and $R_3$ is hydrogen and the other is $C_1$–$C_4$ alkyl optionally substituted by hydroxy; or $R_2$ and $R_3$ are both methyl and the pharmaceutically acceptable salts thereof.

Specific examples of compounds of formula (IA) are:
2-[4-(3-cyanobenzyloxy)benzylamino]-3-hydroxy-N-methylpropanamide;
[2-[4-(3-cyanobenzyloxy)benzyl]-2-methyl-amino]-3-hydroxy-N-methyl-propanamide, if the case either as a single isomer or as a mixture thereof, and the pharmaceutically acceptable salts thereof.

The compounds of formula (I) and (IA) and the pharmaceutically acceptable salts thereof can be obtained by well known processes as described in the above cited international applications. In particular, a compound of formula (IA) and the salts thereof can be obtained by a process comprising:
 a) reacting a compound of formula (II)

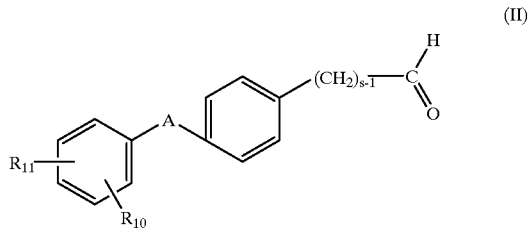

(II)

wherein $R_{10}$, $R_{11}$, A and s are as defined above, with a compound of formula (III)

(III)

wherein $R_2$, $R_3$ and $R_4$ are as defined above, in the presence of a reducing agent thus obtaining a compound of formula (IA) in which $R_1$ is hydrogen; or b) reacting a compound of formula (IV)

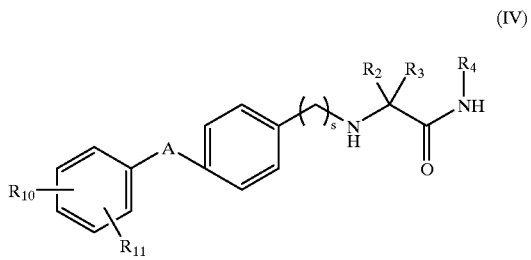

wherein $R_2$, $R_3$, $R_4$, $R_{10}$, $R_{11}$, A and s are as defined above, with a compound of formula (V) or (VI) in this latter case in the presence of a reducing agent

wherein W is a halogen atom; $R'_5$ is $C_1$–$C_4$ alkyl and $R''_5$ is hydrogen or $C_1$–$C_3$ alkyl, thus obtaining a compound of formula (IA) in which $R_1$ is $C_1$–$C_4$ alkyl; and, if desired, converting a compound of formula (IA) into another compound of formula (IA) and/or, if desired, converting a compound of formula (IA) into a pharmaceutically acceptable salt and/or, if desired, converting a salt into a free compound.

All the processes described hereabove are analogy processes and can be carried out according to well known methods in organic chemistry.

A compound of formula (IV) is a compound of formula (IA) in which $R_1$ is hydrogen.

The reaction of a compound of formula (II) with a compound of formula (III) to give a compound of formula (IA) or (IV) is a reductive amination reaction which can be carried out according to well known methods. According to a preferred embodiment of the invention it may be performed under nitrogen atmosphere, in a suitable organic solvent, such as an alcohol, e.g. a lower alkanol, in particular methanol, or in acetonitrile, at a temperature ranging from about 0° C. to about 40° C., in the presence of a reducing agent, the most appropriate being sodium cyanoborohydride.

Occasionally molecular sieves can be added to the reaction mixture for facilitating the reaction.

In a compound of formula (V) the halogen W is preferably iodine. The alkylation reaction of a compound of formula (IV) with a compound of formula (V) can be carried out in a suitable organic solvent, such as an alcohol, e.g. methanol, ethanol or isopropanol, in particular in ethanol, at a temperature ranging from about 0° C. to about 50° C.

The alkylation reaction of a compound of formula (IV) with an aldehyde of formula (VI) can be carried out in a suitable organic solvent, such as an alcohol, e.g. methanol, ethanol or acetonitrile in the presence of a suitable reducing agent, such as sodium cyanoborohydride, at a temperature ranging from about 0° C. to about 30° C.

A compound of formula (IA) can be converted, as stated above, into another compound of formula (IA) by known methods. Process-variant b) above may be regarded as an example of optional conversion of a compound of formula (IA) into another compound of formula (IA).

Also the optional salification of a compound of formula (IA) as well as the conversion of a salt into the free compound may be carried out by conventional methods.

The compounds of formula (II) and (III), (V) and (VI) are known compounds or can be obtained by known methods. When in the compounds of the present invention and in the intermediate-products thereof, groups are present, which need to be protected before submitting them to the hereabove illustrated reactions, they may be protected before being reacted and then deprotected according to methods well known in organic chemistry.

The compounds of formula (I), (IA) and the pharmaceutically acceptable salts thereof are hereinafter defined as "the compounds of the invention" or "the active agents of the invention".

Pharmacology

As stated above, the compounds of the invention are active as analgesic agents, as proven for instance by the fact that they have been found to be active in the formalin test.

Formalin test is a useful tool for obtaining neurogenic inflammation and continuous pain (Shibata et al, Pain, 38: 347–352, 1989).

Formalin produces a distinct biphasic response. The early phase seems to be caused predominantly by C-fibre activation due to peripheral stimulus, while the late phase appears to be dependent on the combination of an inflammatory reaction in the peripheral tissue and functional changes in the dorsal horn of the spinal cord. This functional changes seem to be initiated by the C-fibre barrage during the early phase (Tjolsen et al. Pain 51, 5–17, 1992). Substance P and bradykinin participate in the early phase, while histamine, serotonin, prostaglandins and bradykinin are involved in the late phase.

Formalin Test

Male NMRI mice (22–25 g) were injected with 20 ml of 2.7% solution of formalin into the right hindpaw and placed immediately into observation chambers. The cumulative licking time of the injected paw was recorded in the acute phase (0–5 min) and in the chronic phase (30–40 min) of the nociceptive response of formalin.

The two representative compounds of the invention (S)-2-[4-(3-fluorobenzyloxy)benzylamino]-propanamide, methanesulfonate (internal code PNU 151774E) and (S)-[2-[4-(3-fluorobenzyloxy)benzylamino]-2-methyl-propanamide (internal code PNU 156654E) were administered 60 min before formalin injection at the doses of 7.5, 15.0, 30.0 and 60.0 mg/kg; po. Morphine (5 mg/kg; sc) was used as a positive standard. The activities data analysed by Dunnett's t-test.

Locomotor Activity and Rotarod

The effects of these compounds on locomotor activity and rotarod (a test for evaluating motor co-ordination) were studied in order to exclude changes in these parameters as confounding factors in the evaluation of the formalin response. The locomotor activity test lasted 15 min. Five minutes after testing locomotor activity, the mice were put on the rotarod for 2 min and the number of mice falling within this time were counted.

Compounds PNU 151774E and PNU 156654E were tested at the doses of 7.5, 15.0, 30.0 and 60.0 mg/kg; po. The compounds were administered 60 min before locomotor activity test.

Results

Compounds PNU 151774E and PNU 156654E dose-dependently reduced cumulative licking time in both phases of the formalin test (Table 1) demonstrating analgesic activity without any effect on locomotor or rotarod activity (Table 2).

TABLE 1

Effects of PNU 151774E and PNU 156654E
in the formalin nociception test in mice

| Compound | Dose (mg/kg; po) | Licking time (sec) Acute phase | Licking time (sec) Chronic phase |
|---|---|---|---|
| vehicle | 0.0 | 160.2 ± 2.6 | 74.8 ± 3.7 |
| PNU 151774E | 7.5 | 137.9 ± 2.4[a] | 72.4 ± 2.4 |
|  | 15.0 | 87.9 ± 3.3[a] | 64.3 ± 2.8[b] |
|  | 30.0 | 79.4 ± 3.0[a] | 56.9 ± 2.6[a] |
|  | 60.0 | 63.1 ± 2.6[a] | 38.1 ± 3.6[a] |
| vehicle | 0.0 | 119.4 ± 5.2 | 73.1 ± 6.0 |
| PNU 156654E | 7.5 | 108.4 ± 4.2 | 62.4 ± 3.6 |
|  | 15.0 | 79.7 ± 3.7[a] | 42.1 ± 6.2[a] |
|  | 30.0 | 60.0 ± 2.3[a] | 37.7 ± 6.9[a] |
|  | 60.0 | 44.4 ± 4.2[a] | 17.3 ± 6.6[a] |

[a] = $p < 0.01$;
[b] = $p < 0.05$

TABLE 2

Effects of PNU 151774E and PNU 156654E
on locomotor activity and rotarod

| Compound | Dose (mg/kg; po) | Locomotor activity counts (mean ± sem) | Rotarod co-ordination (mice fallen/total mice) |
|---|---|---|---|
| vehicle | 0 | 2653 ± 163 | 0/10 |
| PNU 151774E | 7.5 | 2908 ± 234 | 0/10 |
|  | 15 | 2795 ± 255 | 0/10 |
|  | 30 | 2347 ± 203 | 0/10 |
|  | 60 | 2240 ± 195 | 0/10 |
| vehicle | 0 | 1976 ± 232 | 0/10 |
| PNU 156654E | 7.5 | 1966 ± 188 | 0/10 |
|  | 15 | 2110 ± 256 | 0/10 |
|  | 30 | 2272 ± 317 | 0/10 |
|  | 60 | 2119 ± 310 | 0/10 |

In view of their biological activity, the compounds of the invention are useful in mammals, including humans, as analgesic agents. In particular they are useful in treating pain associated with damage or permanent alteration of the peripheral or central nervous system, for example peripheral neuropathies, such as trigeminal neuralgia, postherapeutic neuralgia, diabetic neuropathy, raticulopathy glossopharyngeal neuralgia, and neuropathy secondary to metastatic infiltration, adiposis dolorosa, and burn pain; and central pain conditions following stroke, thalamic lesions and multiple sclerosis.

The conditions of a patient in need of an analgesic agent may thus be improved.

The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous injection or infusion.

The dosage depends on the age, weight, conditions of the patient and on the administration route; for example, the dosage adopted for oral administration to adult humans e.g. for the representative compounds of the invention (S)-2-[4-(3-fluorobenzyloxy)benzylamino]-propanamide, methanesulfonate,
(S)-[2-[4-(3-fluorobenzyloxy)benzylamino]-2-methyl-propanamide, and
(S)-[2-[4-(3-cyanobenzyloxy)benzylamino]-3-hydroxy-N-methylpropanamide may range from about 1 to about 500 mg pro dose, from 1 to 5 times daily.

The invention includes pharmaceutical compositions comprising a compound of formula (IA), as an active principle, in association with a pharmaceutically acceptable excipient (which can be a carrier or a diluent). The pharmaceutical compositions containing the compounds of the invention are usually prepared following conventional methods and are administered in a pharmaceutically suitable form.

For example, the solid oral forms may contain, together with the active compound, diluents, e.g. lactose, destrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; desegregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersion for oral administration may be e.g. syrups, emulsions and suspension.

The syrups may contain as carrier, for example, saccharose or saccharose with glycerine and/or mannitol and/or sorbitol.

The suspension and the emulsion may contain as carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusion may contain as carrier, for example, sterile water or preferably they may be in the form of sterile, aqueous, isotonic saline solutions.

The suppositories may contain together with the active compound a pharmaceutically acceptable carrier, e.g. cocoa butter, polyethylene glycol, a polyoxyethylene sorbitan fatty acid ester surfactant or lecithin.

The following examples illustrate but do not limit the invention.

EXAMPLE 1

(S)-2-[4-(3-cyanobenzyloxy)benzylamino]-3-hydroxy-N-methyl-propanamide

To a solution of N-methylserinamide hydrochloride (2 g; 0.0129 mol), in methanol (40 ml), 2 g of powdered 3A molecular sieves are added; after stirring 15' at room temperature, 0.65 g (0.0102 mol) of sodium cyanoborohydride are added in a single portion followed by 2.85 g (0.012 mol) of 4-(3-cyanobenzyloxy)benzaldehyde. The mixture is stirred for 2 hours at room temperature, then filtered and the residue after evaporation is separated by flash-chromatography on silica gel (eluant: chloroform 98: methanol 2: 30% NH4OH 0.2). 2.6 g (63%) of pure titled compound (m.p. 130–134° C.).

$[\alpha]_D$: +12.8 (c=1.25 AcOH)

EXAMPLE 2

(S)-[2-[4-(3-cyanobenzyloxy)benzyl]-2-methyl-amino]-3-hydroxy-N-methyl-propanamide (S)-2-[4-(3-cyanobenzyloxy)benzylamino]-3-hydroxy-N-methyl-propanamide (2 g; 0.0059 mol) is dissolved in methanol (30 ml) and 1.8 g (0.013 mol) of anhydrous potassium carbonate are added to the solution. Methyl iodide (1.5 ml; 0.025 mol) is dropped into the mixture which is stirred for 2 hours at room temperature and then evaporated to dryness. The crude residue is chromatographed on silica gel (eluant:chloroform/methanol; 95/5). 1.88 g (90%) of (S)-[2-[4-(3-cyanobenzyloxy)benzyl]-2-methyl-amino]-3-hydroxy-N-methyl-propanamide are obtained.

Elemental Analysis:

| Atom | Calc. | Found |
|------|-------|-------|
| C    | 67.97 | 67.69 |
| H    | 6.56  | 6.48  |
| N    | 11.89 | 11.98 |

EXAMPLE 3

With the usual methods of pharmaceutical technique, preparation can be made of capsules having the following composition:

| | |
|---|---|
| (S)-2-[4-(3-cyanobenzyloxy)benzylamino]-3-hydroxy-N-methyl -propanamide | 50 mg |
| Talc | 2 mg |
| Corn starch | 2 mg |
| Microcristalline cellulose | 6 mg |
| Magnesium stearate | 1 mg |

What is claimed is:

1. A method of treating pain in a patient in need thereof, said method comprising administering to the patient a medicament comprising an effective amount of an analgesic which is an alpha-aminoamide compound of formula (I)

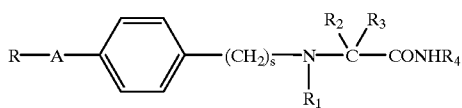

(I)

wherein:
A is a —$(CH_2)_m$—, —$(CH_2)_n$—X— or —$(CH_2)_v$—O— group wherein m is an integer of 1 to 4, n is zero or an integer of 1 to 4, X is —S— or —NH—, and v is zero or an integer of 1 to 5;

s is 1 or 2;

R is a ring or a phenyl ring optionally substituted by one or two substituents independently chosen from halogen, cyano, $C_1$–$C_4$ alkyl, $C_1$–$C_4$ alkoxy and trifluoromethyl;

$R_1$ is hydrogen or $C_1$–$C_4$ alkyl;

one of $R_2$ and $R_3$ is hydrogen and the other is hydrogen or $C_1$–$C_4$ alkyl optionally substituted by hydroxy or phenyl; or $R_2$ and $R_3$ taken together with the carbon atom to which they are linked form a $C_3$–$C_6$ cycloalkyl ring; or $R_2$ and $R_3$ are both methyl;

$R_4$ is hydrogen or $C_1$–$C_4$ alkyl;

or a pharmaceutically acceptable salt thereof;

with the provisos that,
when A is a —$(CH_2)_5$—O— group then s is 1, R is a phenyl group optionally substituted by one or two substituents selected independently from halogen, trifluoromethyl and $C_1$–$C_4$ alkoxy, $R_1$ is hydrogen and one of $R_2$ and $R_3$ is hydrogen and the other is hydrogen or $C_1$–$C_4$ alkyl optionally substituted hydroxy; and when $R_2$ and $R_3$ are both methyl then R is other than a furyl, thienyl or pyridyl ring.

2. A method of treating chronic or neuropathic pain in a patient in need thereof, said method comprising the method according to claim 1.

3. The method according to claim 1, wherein in the compound of formula (I),

A is a group chosen from —$CH_2$—, —$CH_2CH_2$—, —$CH_2$—S—, —$CH_2$—$CH_2$—S— and —$(CH_2)_v$—O— in which v is an integer of 1 to 5;

s is 1 or 2;

R is a phenyl ring optionally substituted by one or two substituents independently chosen from halogen and cyano or a thienyl ring;

$R_1$ is hydrogen or $C_1$–$C_4$ alkyl; one of $R_2$ and $R_3$ is hydrogen and the other is $C_1$–$C_4$ alkyl optionally substituted by hydroxy or phenyl; or $R_2$ and $R_3$ are both methyl; and $R_4$ is hydrogen or $C_1$–$C_4$ alkyl.

4. A method of treating pain in a patient in need thereof, said method comprising administering to the patient a medicament comprising an effective amount of an analgesic which is selected from the group consisting of:

2-[4-(3-fluorobenzyloxy)benzylamino]-2-methyl-propanamide;
2-[4-(3-fluorobenzyloxy)benzylamino]propanamide;
2-(4-benzyloxybenzyulamino)propanamide;
2-[4-(2-fluorobenzyloxy)benzylamino]propanamide;
2-[4-(4-fluorobenzyloxy)benzylamino]propanamide;
2-[4-(2-chlorobenzyloxy)benzylamino]propanamide;
2-[4-(3-chlorobenzyloxy)benzylamino]propanamide;
2-[4-(3-fluorobenzyloxy)benzylamino]-3-hydroxy-N-methylpropanamide;
2-[4-(2-fluorobenzyloxy)benzylamino]-3-hydroxy-N-methylpropanamide;
2-[4-(2-chlorobenzyloxy)benzylamino]-3-hydroxy-N-methylpropanamide;
2-[4-(3-cyanobenzyloxy)benzylamino]-3-hydroxy-N-methylpropanamide;
2-[4-(3-chlorobenzyloxy)phenylethylamino]-propanamide;
2-(4-benzyloxybenzylamino)-3-hydroxy-N-methyl-propanamide;
2-[4-(2-thenyloxy)benzylamino]-propanamide;
2-[4-(3-fluorobenzyloxy)benzylamino]-N-methylpropanamide;
2-[4-(3-fluorobenzyloxy)benzylamino]-3-hydroxy-propanamide;
2-[4-(2-(3-fluorophenyl)ethyloxy)benzylamino]-propanamide;
2-[4-(2-(3-fluorophenyl)ethyl)benzylamino]-propanamide;
2-[N-4-benzyloxybenzyl-N-methyl-amino]-propanamide;
2-[2-(4-(3-chlorobenzyloxy)phenylethyl)amino]-propanamide;
2-[4-benzylthiobenzylamino]-propanamide;
2-[4-(3-phenylpropyloxy)benzylamino]-propanamide;
2-[4-(4-phenylbutyloxy)benzylamino]-propanamide;
2-[4-(5-phylpentyloxy)benzylamino]-propanamide;
2-[4-benzyloxybenzylamino]-3-phenyl-N-methylpropanamide;
2-[4-benzyloxybenzylamino]-3-methyl-N-methylbutanamide, isomers, mixtures and pharmaceutically acceptable salts thereof.

5. A pharmaceutical composition having analgesic activity, comprising a pharmaceutically acceptable excipient and, as an active agent, a compound as defined in claim 1.

6. A method of treating pain in a patient in need thereof, said method comprising administering to the patient an effective amount of an alpha-aminoamide compound of formula (I), or a pharmaceutically acceptable salt thereof.

7. A compound which is an alpha-aminoamide of formula (IA)

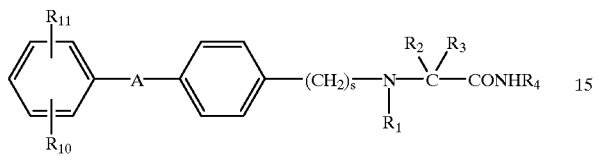

wherein:
A is a —$(CH_2)_m$— or —$(CH_2)_n$—E— group wherein m is an integer of 1 to 4, n is zero or an integer of 1 to 4 and E is —O—, —S— or —NH—;
s is 1 or 2;
one of $R_{10}$ and $R_{11}$ is cyano and the other is independently selected from hydrogen, halogen, cyano, $C_1$–$C_4$ alkyl, $C_1$–$C_4$ alkoxy and trifluoromethyl;
$R_1$ is hydrogen or $C_1$–$C_4$ alkyl;
one of $R_2$ and $R_3$ is hydrogen and the other is hydrogen or $C_1$–$C_4$ alkyl optionally substituted by hydroxy or phenyl; or $R_2$ and $R_3$ taken together with the carbon atom to which they are linked form a $C_3$–$C_6$ cycloalkyl ring; or $R_2$ and $R_3$ are both methyl;
$R_4$ is hydrogen or $C_1$–$C_4$ alkyl ring; or a pharmaceutically acceptable salt thereof.

8. A compound according to claim 7, wherein
A is a group —$CH_2$—O— or —$CH_2$—$CH_2$—O—,
s is 1;
one of $R_{10}$ and $R_{11}$ is cyano and the other is hydrogen, cyano or halogen; and
one of $R_2$ and $R_3$ is hydrogen and the other is $C_1$–$C_4$ alkyl optionally substituted by hydroxy; or $R_2$ and $R_3$ are both methyl.

9. A compound selected from the group consisting of:
2-[4-(3-cyanobenzyloxy)benzylamino]-3-hydroxy-N-methylpropanamide; and
2-[4-(3 cyanobenzyloxy)benzyl]-2-methyl-amino]-3-hydroxy-N-methyl-propanamide; isomers, mixtures and pharmaceutically acceptable salts thereof.

10. A pharmaceutical composition comprising a pharmaceutically acceptable excipient and, as an active agent, a compound as defined in claim 7.

11. A method of treating pain in a patient in need thereof, said method comprising administering to the patient an analgesic which comprises an effective amount of the compound according to claim 7 and a pharmaceutically acceptable carrier.

12. A method of treating pain in a patient in need thereof, said method comprising administering to the patient an effective amount of the compound according to claim 7.

* * * * *

UNITED STATES PATENT AND TRADEMARK OFFICE
CERTIFICATE OF CORRECTION

PATENT NO.    : 6,306,903 B1
DATED         : October 23, 2001
INVENTOR(S)   : Pevarello et al.

It is certified that error appears in the above-identified patent and that said Letters Patent is hereby corrected as shown below:

Column 9, line 34 through Column 10, line 6,
Please delete current claim 1 and replace with the following:

--1.    A method of treating pain in a patient in need thereof, said method comprising administering to the patient a medicament comprising an effective amount of an analgesic which is an alpha-aminoamide compound of formula (I)

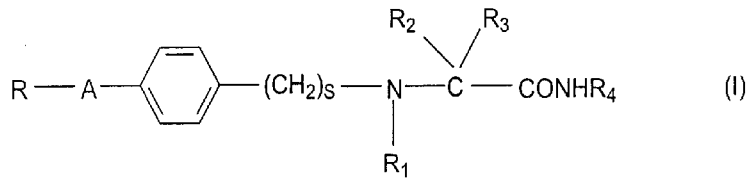

wherein:

A is a $-(CH_2)_m-$, $-(CH_2)_n-X-$ or $-(CH_2)_v-O-$ group wherein m is an integer of 1 to 4, n is zero or an integer of 1 to 4, X is -S- or -NH-, and v is zero or an integer of 1 to 5;

s is 1 or 2;

R is a ring or a phenyl ring optionally substituted by one or two substituents independently chosen from halogen, cyano, $C_1$-$C_4$ alkyl, $C_1$-$C_4$ alkoxy and trifluoromethyl;

UNITED STATES PATENT AND TRADEMARK OFFICE
CERTIFICATE OF CORRECTION

PATENT NO. : 6,306,903 B1
DATED : October 23, 2001
INVENTOR(S) : Pevarello et al.

It is certified that error appears in the above-identified patent and that said Letters Patent is hereby corrected as shown below:

<u>Columns 9 and 10 (cont'd),</u>

$R_1$ is hydrogen or $C_1$-$C_4$ alkyl;

one of $R_2$ and $R_3$ is hydrogen and the other is hydrogen or $C_1$-$C_4$ alkyl optionally substituted by hydroxy or phenyl; or $R_2$ and $R_3$ taken together with the carbon atom to which they are linked form a $C_3$-$C_6$ cycloalkyl ring; or $R_2$ and $R_3$ are both methyl;

$R_4$ is hydrogen or $C_1$-$C_4$ alkyl;

or a pharmaceutically acceptable salt thereof;

with the proviso that, when A is a -$(CH_2)_5$-O- group then s is 1, R is a phenyl group optionally substituted by one or two substituents selected independently from halogen, trifluoromethyl and $C_1$-$C_4$ alkoxy, $R_1$ is hydrogen and one of $R_2$ and $R_3$ is hydrogen and the other is hydrogen or $C_1$-$C_4$ alkyl optionally substituted hydroxy. --

Signed and Sealed this

Twenty-seventh Day of April, 2004

JON W. DUDAS
*Acting Director of the United States Patent and Trademark Office*